United States Patent [19]

Herbst et al.

[11] Patent Number: 4,683,896
[45] Date of Patent: Aug. 4, 1987

[54] METHOD FOR FIXING AN ELECTRICAL ELECTRODE TO BONE TISSUE

[75] Inventors: Ewa Herbst, Jungfrudansen 24, 171 56 Solna; Lars I. Botvidsson, Järfälla, both of Sweden

[73] Assignee: Ewa Herbst, Solna, Sweden

[21] Appl. No.: 671,081

[22] Filed: Nov. 13, 1984

[51] Int. Cl.[4] ............................................. A61N 1/04
[52] U.S. Cl. ................................ 128/785; 128/419 F; 128/642
[58] Field of Search ............ 128/419 F, 642, 784–786, 128/82.1

[56] References Cited

U.S. PATENT DOCUMENTS

| 3,918,440 | 11/1975 | Kraus | 128/419 F X |
| 4,141,365 | 2/1979 | Fischell et al. | 128/642 |
| 4,207,903 | 6/1980 | O'Neill | 128/785 |
| 4,246,908 | 1/1981 | Inagaki et al. | 128/748 |
| 4,333,469 | 6/1982 | Jeffcoat et al. | 128/419 F |
| 4,442,846 | 4/1984 | Brighton et al. | 128/419 F X |
| 4,461,300 | 7/1984 | Christensen | 128/419 F |
| 4,467,817 | 8/1984 | Harris | 128/785 X |
| 4,506,674 | 3/1985 | Brighton et al. | 128/419 F |

OTHER PUBLICATIONS

Lavine et al., "Electric Enhancement of Bone Healing"; Science, vol. 175, 3-1972, pp. 1118-1121.
Friedenberg et al.; "Electro-Osteograms of Long Bones of Immature Rabbits"; J. of Dent. Res., 5/1971, pp. 635–639.

Primary Examiner—Lee S. Cohen
Assistant Examiner—Angela D. Sykes
Attorney, Agent, or Firm—Burns, Doane, Swecker & Mathis

[57] ABSTRACT

The invention relates to a method for attaching, through soft tissue, an electric electrode to bone tissue (hard tissue), in which the electrode is provided with a rigid electrode tip and a highly flexible cable which is connected to the electrode tip and which is electrically insulated against surrounding soft tissue. The method comprises the following steps, given by way of example:

(a) applying one end (3a) of an elongated guide means (1) having a longitudinally extending channel (2) to an outer surface (4) of soft tissue (5) immediately adjacent a fracture location (6) of bone tissue;
(b) moving one end (3a) of the elongated member through the soft tissue towards said bone tissue;
(c) introducing through the channel (2) firstly an electrode having a rigid electrode tip (20) and a flexible cable (25) connected thereto, and secondly a tube (25) which embraces the cable and which coacts with the electrode tip via coupling means;
(d) displacing the tube (25) relative to the guide means (1) in a manner to move the electrode tip (20) towards the hard tissue;
(e) causing the electrode tip (20) to penetrate the bone tissue, by exerting a force on the tube (25) in a direction towards the bone tissue (7); and
(f) removing the tube (25) and the guide means (1) in a manner such as to leave a part (22a) of the flexible cable exposed above the outer surface (14) of the soft tissue (5), such as to enable the cable to be connected to an electric current or voltage source.

18 Claims, 7 Drawing Figures

U.S. Patent    Aug. 4, 1987    4,683,896
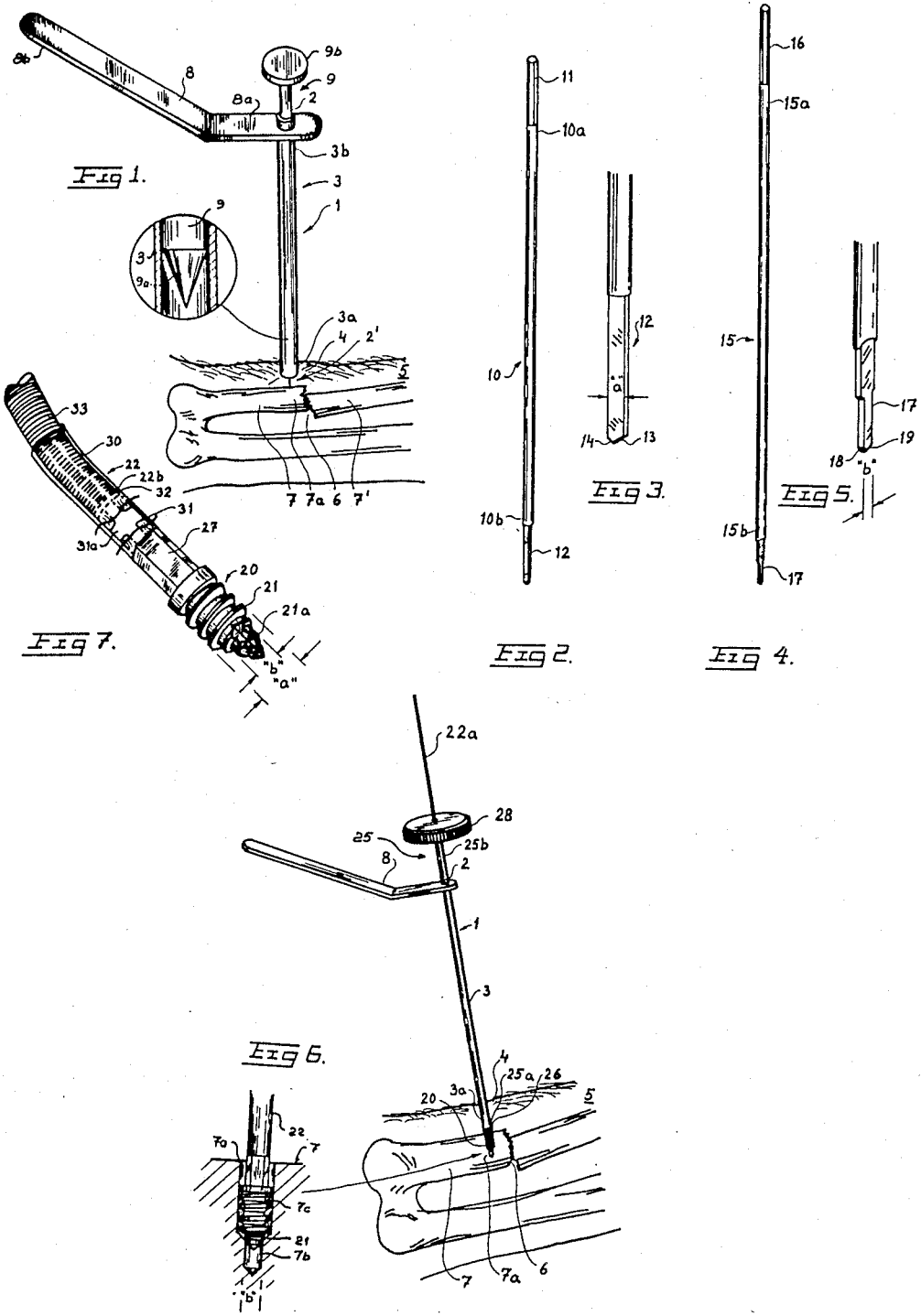

METHOD FOR FIXING AN ELECTRICAL ELECTRODE TO BONE TISSUE

TECHNICAL FIELD

The present invention relates to a method for fixing an electrode to bone tissue or hard tissue for electrically stimulating a healing process therein, the electrode being of the kind having a rigid electrode tip and a highly flexible electrically insulated cable attached thereto.

The invention also relates to an electrical electrode with which the method can be carried out.

BACKGROUND ART

Several devices are known to the art by means of which healing of bone tissue is promoted by electrically stimulating the bone tissue with the aid of one or more electrodes applied to the fracture point of a broken limb, these devices including means whereby an electric current or an electric voltage can be applied to the electrode.

Such devices and electrodes are normally used to avoid the necessity of carrying out surgery on the damaged bone. To this end it is known to affix one or more electrodes in the region adjacent the fracture surface and to connect the electrodes to an electrical stimulating device, located externally on a fractured limb being treated, or on a plaster cast placed therearound.

A variety of such electrodes, which are affixed to bone tissue and connected to a source of electric current or voltage for the purpose of stimulating a bone healing process (osteogenesis), are known to the art.

Electrodes used within the medical field for this purpose can be divided into two separate categories, each relating to the nature of the tissue to which electrodes are to be applied and the manner in which they are used. Thus, electrodes of the first category are particularly designed for insertion into soft tissue and there to be firmly and reliably held in good electrical contact with the soft tissue, normally muscle tissue, these electrodes normally being used to evaluate muscle tension etc.. The electrodes belonging to the second category are particularly designed for attachment to bone tissue or hard tissue, so as to be firmly seated in good electrical contact with the hard tissue while being insulated from the soft tissue, in order to stimulate osteogenesis.

The present invention relates to the second category of electrode.

The U.S. Patent Specification No. 3,842,841, which relates to an electrode of this second category, discloses the use of an external anode which is secured to the outer surface of the skins and a cathode which comprises a long rigid stainless steel wire covered with an electrically insulated material, such as polytetrafluoroethylene. This steel wire is pressed through the skin, i.e. percutaneous insertion, whilst screening the damaged area with X-rays (radioscopy), and pushed into the bone close to a fracture or area of diseased bone to be treated.

It is also known to use a hand drill to assist the insertion of these rigid electrodes some short distance into the bone tissue, so that the electrode tip is firmly seated therein.

DISCLOSURE OF THE PRESENT INVENTION

TECHNICAL PROBLEM

With reference to the present state of the art as described above it is obvious that one technical problem encountered in this field is that of providing a method and an electric electrode by means of which an electrode tip can be firmly attached to bone tissue with the aid of simple means, whilst still permitting the use of a flexible, electrically insulated connecting cable extending between a source of electric current or electric voltage and the electrode tip.

A further technical problem is that of being able to find ways and means whereby the irritation experienced as the skin is penetrated, due to muscle contraction and prevalent with steel-wire bone electrodes, can be eliminated.

With such electrode there is a grave risk that the rigid steel wire will break off within the bone, if an excessive load is applied thereto. Consequently, a further technical problem in this art is one of eliminating this risk.

Another technical problem related hereto is to be found in the provision of a method and an electrode having a rigid electrode tip and a flexible connecting cable which can be provided with a non-breakable connection between the electrode tip and the cable, since this would eliminate the need of surgery to remove any part of a broken electrode still attached to the tissue and extending therebeyond, such surgery often being necessary with present day methods and electrodes.

Still another technical problem is that of providing a method by which a rigid electrode having a flexible connecting cable can be attached to bone tissue through a pre-bore, where the electrode tip is fully inserted into the bone tissue and can be left there without discomfort to the patient.

A further technical problem is one of designing an electrode which fulfills the aforementioned requirements and which enables the connecting cable to be readily removed, without surgical involvement, when it is considered that the rigid electrode tip can be left in the bone tissue.

A further technical problem is one of providing means whereby an electrode tip can be introduced into bone tissue in a direction determined by a guide tube firmly held by soft tissue.

Still another technical problem is one of enabling a pre-bore to be formed in bone tissue with the aid of simple means, and of enabling the electrode tip to be readily introduced into such a pre-bore.

SOLUTION

The present invention affords a solution to the aforesaid technical problems, by providing a method which enables the rigid tip of an electrode connected to a highly flexible connecting cable insulated electrically against surrounding softer tissue, to be attached to bone tissue (hard tissue). Thus, when practising the present invention (a) one end of an elongated guide means having an axially extending channel which is open at both ends thereof is applied to an outer surface of muscle tissue immediately adjacent the bone tissue located in the region of a bone fracture;

(b) one end of the elongated guide means is pressed through the soft muscle tissue, so that said tissue forms a guide for said means;

(c) there is introduced through the channel of the guide means firstly an electrode having a rigid electrode tip and a highly flexible electric cable connected to the tip and to an electric current or voltage source, and secondly a tube which embraces the electric cable and which co-acts with the electrode tip via coupling means;

(d) the electrode tip is displaced by effecting relative movement between the tube and the guide means, against the hard tissue;

(e) the tube is pressed against the bone tissue such as to cause the electrode tip to penetrate said tissue; and (f) the tube and the guide means are removed so that the part of the electric cable extending above the outer surface of the muscle tissue can be connected to said electrical current or voltage source.

According to the invention there is arranged in the channel a pointed member which extends beyond one end thereof when it is pushed through the soft tissue. Optionally, the pointed member may be pressed in a manner to plastically deform the bone tissue, so as to form a part which co-acts with the electrode tip.

In accordance with one advantageous feature of the invention, the electrode tip is inserted into the bone tissue with the aid of an axially directed force, wherewith the aid of rotation movement applied to a pointed part provided with cutting screw-threads.

The scope of the invention also embraces a method for attaching an electric electrode to exposed bone tissue, in which the electrode is provided with a rigid electrode tip and a highly flexible cable connected thereto, by (a) forming in the bone tissue a hole having a depth which exceeds the longitudinal extension of the electrode tip and a cross-sectional area which is only slightly smaller than the cross-sectional area of the electrode tip, and (b) by causing the electrode tip to co-act with the aforesaid hole in a manner such as to enclose the electrode tip in said hole.

According to one embodiment the bore may have a narrow outermost part and a broader part, in which the cross-sectional area of the narrow part is somewhat smaller than the cross-sectional area of the electrode tip, while the cross-sectional area of the broader part is equal to or somewhat greater than the cross-sectional area of the electrode tip.

In accordance with another embodiment a drill is inserted through a channel in a guide means for forming a desired hole in the bone tissue. When the electrode tip is provided with cutting screw-threads, the diameter of the drill is smaller than the diameter of the screw-threaded part of the electrode tip. The drill is removed prior to inserting the electrode and the tube through the channel.

The present invention also relates to an electric electrode designed for application to bone tissue (hard tissue) and having a rigid electrode tip. The electrode tip is connected to a highly flexible electrically insulated connecting cable.

The electric electrode conveniently exhibits a specific connection between electrode tip and connecting cable, this connection being so formed that when a pulling force is applied in the longitudinal direction of the connecting cable from the electrode tip, the cable will be moved out of co-action with said tip.

The electrode tip is suitably provided, adjacent the point at which it is connected to the cable, with a fitting which is able to co-act with one end of the tube to prevent rotation thereof. The connecting cable comprises a helically wound wire enclosed in an electrically insulating sleeve or sheath.

Both the helically wound wire and the insulating sleeve are firmly secured in relation to the electrode tip. The wire can be removed by withdrawing it from the insulating sleeve. The sleeve can be removed by pulling the same in a direction away from the electrode tip, therewith leaving the electrode tip firmly screwed into the bone tissue.

As will be understood, when wishing to remove the electrode completely there is nothing to prevent the connecting cable from being stretched somewhat away from the electrode tip and the tube being caused to embrace the cable, so that one end of the tube can be displaced down through the soft tissue and optionally through the bone tissue against the electrode, and there caused to co-act with the fitting or coupling means formed on the electrode tip, thereby to enable the electrode tip to be rotated out of the bone tissue, to permit the connecting cable and the electrode tip to be removed.

ADVANTAGES

Those advantages primarily characteristic of a method and an electrode in accordance with the present invention are to be found in the possibilities provided thereby of applying a rigid electrode tip to bone tissue and, when the electrode tip is connected to the bone tissue, of enabling a flexible cable to be connected to an electrical current or voltage source, for the electrical stimulation of the bone healing process.

The primary characterizing features of a method according to the present invention are set forth in the characterizing clauses of the following claims 1-9, while the primary characterizing features of an electrode according to the invention are defined in the characterizing clauses of the following claims 10-14.

SHORT DESCRIPTION OF THE DRAWINGS

An embodiment illustrating the significant characterizing features of an electric electrode and a method according to the invention for attaching the electric electrode to bone tissue will now be described with reference to the accompanying drawings, said embodiment being that preferred at present, in which drawings FIG. 1 is a perspective view of a guide means, one end of which is applied to the outer surface of soft tissue located adjacent a bone fracture;

FIG. 2 is a side view of a first embodiment of a drill which can be used to drill a hole in bone tissue;

FIG. 3 illustrated the drill bit in larger scale of the drill illustrated in FIG. 2;

FIG. 4 is a side view of a second embodiment of a drill for drilling a hole in bone tissue;

FIG. 5 illustrates in larger scale the drill bit of the drill shown in FIG. 4;

FIG. 6 illustrates in perspective the manner of applying one end of the guide means to the outer surface of bone tissue or hard tissue, and further illustrates a manner of screwing an electric electrode percutaneously to bone tissue; and FIG. 7 is a perspective view, in larger scale, of the electrode tip of an electric electrode with a connecting cable connected thereto.

DESCRIPTION OF PREFERRED EMBODIMENTS

FIG. 1 illustrates in perspective a guide means generally shown at 1, comprising an elongated guide tube 3 having extending axially therein a channel 2 which is open at both ends thereof. One end, 3a, of the guide tube 3 is intended to be placed against an outer surface 4 of soft tissue 5, in the immediate vicinity of a fracture 6 located between two shafts of bone 7, 7', and further comprising holder means 8 which is connected at one end 8a thereof to the upper end 3b of the guide tube 3, and the other end 8b of which serves as a handgrip.

The holder means 8 connected to the end 3b of the guide tube is intended for controlling the alignment of the guide means 1, such that an extension 2' of the channel 2 is positioned in or within a region of bone tissue where the electrode tip is to be applied. This area is referenced 7a in FIG. 1 and forms a point on the bone tissue. The region where the electrode tip should be applied can be determined by X-ray screening or radioscopy, in a known manner. The guide tube 3 is then pressed through the skin, so that the end 3a of the tube is located at the point or location 7a.

In the illustrated embodiment, insertion of the tube 3 through the skin is facilitated by means of a needle-like member 9 having a pointed part 9a and being arranged for axial movement in said channel. The end of the member 9 remote from said pointed part is provided with a push plate 9b. The length of the needle-like member 9 is slightly greater than the length of the guide tube 3, and in its initial position the member 9 is withdrawn in the channel of the guide means 3.

In this position, the soft tissue 5 forms a means for guiding and positioning the guide tube 3.

When the pointed part 9a is pressed against the location 7a on a bone shaft, the bone is plastically deformed to provide a gripping surface for a drill and/or a screw having self-cutting threads. The needle-like piercing member 9 is removed when the guide tube has been inserted to the desired position in the soft tissue. Although the present invention can be applied to secure electrode tips to bone tissue without previously drilling a hole therein, it has been found that certain problems can occur when no such pre-bore is formed. One such problem is the risk of the bone tissue splitting.

In order to avoid this problem, there is preferably formed in the bone tissue 7 a pre-bore having a diameter which is slightly smaller than the outer diameter of the electrode tip. To this end there is provided in accordance with the invention a drill having the form illustrated in FIG. 4.

When the electrode tip is to be embedded deep in the bone tissue, there is used a pre-bore formed by a drill of the kind illustrated in FIG. 2. The drill illustrated in FIG. 2 is generally referenced 10 and has at one end 10a thereof connecting means 11 for connecting the drill to a drilling machine, while the other end 10b of the drill carries a drill bit 12. The drill bit 12 is shown in larger scale in FIG. 3, and has edge portions 13,14, where the distance "a" is such as to substantially correspond to the distance "a" in FIG. 7. Thus, the distance "a" between the surface flanking said edge portions 13,14 shall correspond to the maximum width of the electrode tip, or shall be slightly greater than said width.

When attaching the actual electrode tip to bone tissue, it is proposed, in accordance with the invention, that there is formed a pre-bore with the aid of a drill 15, which is provided at one end 15a thereof with connecting means 16 for connecting the drill to a drilling machine, and which has at the other end 15b thereof a drill bit 17. The drill bit 17 is shown in larger scale and in more detail in FIG. 5, from which the orientation of edge portions 18, 19 can be seen. The drill 15 is intended to form in bone tissue 7 a hole 7b having a diameter "b", said hole being smaller than the hole 7c of diameter "a".

The narrower part of the drill 15 is arranged for co-action with the electrode tip 20 via a tensioning or clamping action.

The electrode tip may be provided with barbs for solely pressing the tip into the hole.

In the illustrated embodiment, the electrode tip 20 is provided with self-cutting screws, and the distance or diameter "b" shall be adapted to the root diameter of the screw thread.

Positioning of the guide means 1 in the soft tissue 5 ensures that the two drills 15 and 10 are aligned in one and the same direction.

As will be seen more clearly from FIG. 6, with the guide tube 3 located in the desired position and guided by the soft tissue 5, there is now passed through the channel 2 in the guide tube 3 firstly an electrode 20 having a self-tapping, rigid electrode tip 21 and a highly flexible connecting cable 22 connected thereto, and secondly a tube 25 which embraces the cable and which co-acts with the electrode tip via coupling means, the lower part 25a of the tube 25 being provided with said coupling means 26 arranged to co-act with corresponding coupling means 27 provided on the upper part of the electrode tip 20, the coupling means 27 of this embodiment having the form of a regular hexagon. This is shown in more detail in FIG. 7.

The upper part 25b of the tube 25 is provided with a knob 28, by means of which the electrode tip 20 can be caused to rotate and a downwardly directed force can be exerted for screwing the tip into the bone or bone tissue 7.

It will also be seen from FIG. 6 that the tube 25 and the guide means 1 can be moved relative to one another, such that the electrode tip 20 will pass through the channel 2 and beyond the soft tissue 5, to co-act with the bone tissue.

Thus, the electrode tip 21 can be screwed into the bone tissue 7, by rotating the tube 25 with the aid of knob 28, while exerting pressure against the bone tissue.

By then removing the tube 25 and the guide means 1, preferably together, part of the flexible cable extending above the outer surface 4 of the soft tissue 5 can be connected to a source of electric current or voltage, not shown. This part of the flexible cable has been referenced 22a.

The bore comprising holes 7b and 7c should be drilled to a depth such as to enclose the whole of the electrode tip 20. As will be understood, the hole can be made deeper than that illustrated in FIG. 6.

FIG. 7 illustrates in larger scale in relation to FIG. 6 the pointed part of the electric electrode according to the invention, arranged to be firmly screwed into bone tissue 7. The electrode is provided with a rigid electrode tip 21, having the form of a self-tapping or self-cutting screw. The electrode tip is also provided with a cutting edge 21a, having a cavity in which bone cuttings are accommodated. Connected to the electrode 20 is a flexible connecting cable 22 which is electrically insulated against surrounding soft tissue. This insulation is referenced 30 and has the form of an insulating sleeve or sheath.

Arranged between the electrode tip 20 and the cable 22 is an electrical connection so constructed that when pulling in the direction of cable 22, the end part 22b of the cable will separate from the connecting part 31 of the electrode tip 20.

As will be seen from the Figure, the electrode tip 20 is provided, adjacent the connecting part 31, with coupling means or a fitting 27 arranged to co-act with one end 25a of the tube 25 in a manner to hold the same against axial rotation, in a manner known per se, via a corresponding coupling means provided on said one end.

The cable 22 comprises a helically and tightly wound wire 33 encased in an electrically insulating hose 30. Both the helically wound wire 33 and the hose 30 are fixed in relation to the part 31 of the electrode tip 20, by clamping the wire 33 by means of a sleeve 31a and by threading the electrically insulating hose 30 over the sleeve 31a. When the wire 33 is removed by withdrawing it from the hose or sheath 30, complete withdrawal of the wire will also release the hose 30 from its co-action with the sleeve 32, permitting the hose 22 to be also removed. Both the wire and the hose can be removed by pulling the same away from the electrode tip.

In so doing, the electrode tip 20 will be left seated in the bone tissue 7, fully embraced thereby.

When wishing to also remove the electrode tip 20 from the bone tissue 7, it is proposed in accordance with the invention that the connecting cable 22 is stretched up from the electrode tip 21 and that the tube 25 is passed over the cable 22 such that the coupling means 26 on the tube-end 25a are brought into co-action with the coupling means 27 for the electrode tip 20, so as to enable the electrode to be fully removed from the bone tissue 7, by rotating the electrode tip 20 in a direction in which it is screwed out of said bone tissue, without requiring surgical intervention.

As will be understood, the drills 10 and 15 may each be provided with graduations (mm-scale), to enable the depth of the drilled hole to be established in relation to the upper edge part of the guide tube 3.

As will be understood, the invention is not restricted to the aforedescribed embodiments, given by way of example only, and that the modifications can be made within the scope of the following claims.

We claim:

1. A method for attaching through soft tissue an electrode to bone tissue, said electrode having a rigid electrode tip and a flexible electric cable connected to the electrode tip and being electrically insulated against surrounding soft tissue, comprising the steps of:
    applying one end of an elongated guide means having a longitudinally extending channel to an outer surface of soft tissue adjacent a selected location of bone tissue;
    moving the one end of the elongated guide means through the soft tissue towards the bone tissue;
    preforming a hole in the bone tissue by introducing a member through said channel;
    introducing through the channel an electrode having a rigid electrode tip, a flexible cable connected thereto and means for stiffening the cable, said cable stiffening means releasably connected with said electrode tip;
    displacing the cable stiffening means through the guide means so as to move the electrode tip into contact with the bone tissue adjacent said hole;
    threading the electrode tip into the bone tissue adjacent said hole so that said electrode tip is located in the bone tissue; and
    removing the stiffening means and the guide means so as to leave a part of the flexible cable exposed above the outer surface of the soft tissue, whereby the cable may be connected to an electric current or voltage source and said electrode tip may remain in the bone tissue after treatment.

2. The method according to claim 1, further comprising the steps of arranging a pointed member in the channel and extending the pointed member beyond the one end of the elongated guide means when said elongated guide means is moved through the soft tissue.

3. The method according to claim 2, wherein the step of preforming a hole includes pressing the pointed member so as to plastically deform the bone tissue to thereby form theron a location adapted for coaction with the electrode tip.

4. The method according to claim 1, wherein the step of preforming a hole includes applying an axially directed pressure force to the electrode tip with the cable stiffening means, so that said electrode tip penetrates the bone tissue.

5. The method according to claim 1, wherein the step of preforming a hole includes introducing a drill through the channel to drill a hole into the bone tissue and removing the drill from the channel, the drill having a narrow outermost part and a broader part, the cross-sectional area of the narrow part being smaller than a cross-sectional area of the electrode tip, the cross-sectional area of the broader part being equal to or greater than the cross-sectional area of the electrode tip.

6. The method according to claim 1, wherein the step of preforming a hole includes introducing a drill through the channel in the guide means for the purpose of drilling a hole in the bone tissue.

7. The method according to claim 6, wherein the electrode tip is provided with cutting screwthreads and a diameter of the drill is smaller than a diameter of the threaded part of the electrode tip, the drill being removed before the electrode and the cable stiffening means are inserted through the channel.

8. A method according to claim 1, wherein the cable stiffening means is in the form of a tube which embraces the cable and coacts with the electrode tip through coupling means.

9. The method according to claim 1, wherein said step of preforming a hole includes introducing through said channel a first drill member having an end portion adapted to cut a first hole portion with a width at least equal to a maximum width of said electrode tip and introducing through said channel another drill member adapted to cut a second hole portion which is narrower than said maximum width of said electrode tip, whereby threading of the electrode tip into the bone tissue may be facilitated.

10. The method according to claim 9, wherein said threading step includes manually rotating said cable stiffening means with the aid of a knob provided on the cable stiffening means.

11. The method according to claim 10, wherein the step of removing the cable stiffening means and the guide means includes pulling the cable stiffening means and the guide means in a direction away from the bone tissue, whereby said cable stiffening means is released from said electrode tip.

12. The method according to claim 11, further comprising the steps of treating the bone tissue with said electrode tip and after said treating step, removing the cable from the electrode tip by withdrawing a wire portion of the cable from an insulating sleeve of the cable and subsequently withdrawing the insulating sleeve by pulling the insulating sleeve away from the electrode tip, whereby said electrode tip remains in the bone tissue after treatment.

13. The method according to claim 12, wherein the threading step includes positioning said electrode tip entirely within the bone tissue.

14. The method according to claim 1, wherein said threading step includes manually rotating said cable stiffening means with the aid of a knob provided on the cable stiffening means.

15. The method according to claim 1, wherein the threading step includes positioning said electrode tip entirely within the bone tissue.

16. The method according to claim 1, wherein the step of removing the cable stiffening means and the guide means includes pulling the cable stiffening means and the guide means in a direction away from the bone tissue, whereby said cable stiffening means is released from said electrode tip.

17. The method according to claim 1, further comprising the steps of treating the bone tissue with said electrode tip and after said treating step, removing the cable from the electrode tip by withdrawing a wire portion of the cable from an insulating sleeve of the cable and subsequently withdrawing the insulating sleeve by pulling the insulating sleeve away from said electrode tip, whereby the electrode tip remains in the bone tissue after treatment.

18. The method according to claim 1, further comprising the step of removing the electrode tip by passing the cable stiffening means along the flexible cable until the cable stiffening means reconnects with the electrode tip, unscrewing the electrode tip from the bone tissue with the cable stiffening means and withdrawing the electrode tip, the cable stiffening means and the flexible cable through the soft tissue.

* * * * *